(12) United States Patent
Hara et al.

(10) Patent No.: US 7,641,639 B2
(45) Date of Patent: Jan. 5, 2010

(54) BODY FLUID SUCTION RESERVOIR

(75) Inventors: Kei Hara, Akita (JP); Yukihiko Sakaguchi, Akita (JP)

(73) Assignee: Sumitomo Bakelite Company, Ltd., Tokyo (JP)

( * ) Notice: Subject to any disclaimer, the term of this patent is extended or adjusted under 35 U.S.C. 154(b) by 733 days.

(21) Appl. No.: 10/534,859

(22) PCT Filed: Nov. 26, 2003

(86) PCT No.: PCT/JP03/15100

§ 371 (c)(1),
(2), (4) Date: May 13, 2005

(87) PCT Pub. No.: WO2004/047886

PCT Pub. Date: Jun. 10, 2004

(65) Prior Publication Data

US 2006/0015078 A1    Jan. 19, 2006

(30) Foreign Application Priority Data

Nov. 28, 2002  (JP) .............................. 2002-346170
Dec. 16, 2002  (JP) .............................. 2002-363656

(51) Int. Cl.
*A61M 1/00*   (2006.01)
*F01B 19/00*  (2006.01)
*A61B 5/00*   (2006.01)

(52) U.S. Cl. ........................ 604/319; 604/321; 604/323; 604/326; 604/327; 92/34; 600/573

(58) Field of Classification Search .................. 604/6.1, 604/6.11, 6.15, 119, 133, 134, 541, 543, 604/544, 319, 323, 322, 326; 600/573; 92/34
See application file for complete search history.

(56) References Cited

U.S. PATENT DOCUMENTS

| 3,299,839 | A | * | 1/1967 | Nordbak ...................... 108/152 |
| 4,349,015 | A | * | 9/1982 | Alferness ...................... 601/41 |
| 4,981,474 | A |   | 1/1991 | Bopp et al. |
| 5,345,929 | A | * | 9/1994 | Jansson et al. ......... 128/205.13 |
| 5,551,849 | A | * | 9/1996 | Christiansen ................ 417/472 |

FOREIGN PATENT DOCUMENTS

| EP | 0048164 A1 | 3/1982 |
| JP | 42-16138   | 9/1967 |
| JP | 49-21037   | 5/1974 |
| JP | 50-84090   | 7/1975 |
| JP | 57-81346   | 5/1982 |
| JP | 61-131751  | 6/1986 |

* cited by examiner

*Primary Examiner*—Leslie Deak
*Assistant Examiner*—Adam Marcetich
(74) *Attorney, Agent, or Firm*—Smith, Gambrell & Russell, LLP

(57) ABSTRACT

The present invention provides a body fluid suction reservoir including a flexible bag, two plates for supporting the bag, and a spring put between the two plates. The body fluid suction reservoir further includes a lock having a hook and a release part and consisting of a member different from the two plates, by which lock the spring is held in a state compressed between the two plates, and the held state is releasable. The lock has flexibility and is held by one of the plates so as to be deformable from a first state in which the hook is engaged with the other plate to a second state in which the hook is not engaged, and the lock is urged to take the first state.

9 Claims, 20 Drawing Sheets

BODY FLUID SUCTION RESERVOIR

TECHNICAL FIELD

The present invention relates to a portable body fluid suction reservoir used to suck and evacuate body fluid from a wound cavity of a human body to improve the adhesiveness of tissue in the wound cavity, and thereby accelerate recovery.

BACKGROUND ART

Conventionally, it has been known to use a body fluid suction reservoir in order to suck in and evacuate body fluid from a wound cavity of a human body. In this case, one end of a tube is inserted into the wound cavity to evacuate and lead the body fluid, and the other end of the tube is connected to a suction reservoir, whereby the body fluid in the wound cavity is collected and stored in the suction reservoir by negative pressure generated in the suction reservoir.

As a mechanism for generating the negative pressure in the suction reservoir, there have been known a mechanism disclosed in JP-A-57-81346 in which a container with an extensible elastic member built-in (such as a spring, or rubber) is previously compressed, in other words, the elastic member is contracted to previously reduce the internal volumetric capacity, so that negative pressure is generated in the container due to restoring force of the elastic member to suck in and collect body fluid, and a mechanism disclosed in JP-A-50-84090 and 61-131751 for example, in which an expandable and extensible elastic member (a balloon or a diaphragm, for example) is provided in a rigid container, and is previously expanded by exhausting gas from the rigid container using internal air supply, exhaust, or other dynamic means, so that negative pressure is generated in the container due to contractive force of the elastic member to suck in and collect body fluid.

Since the former mechanism starts to suck in a state where the container is squashed, it is very compact especially at the beginning of the suction in comparison with the latter mechanism, and has an advantage that it is superior in portability because it does not take much space when it is set to a patient. Further, the former mechanism is provided with a lock means for keeping the container in the squashed state and thus, can contribute to reducing the transferring and storing costs thereof. However, since the suction apparatus disclosed in JP-A-57-81346 is made to release the lock means by folding a hinge portion of a plate, there is a possibility that the lock may be easily released due to external force even in a state where the suction apparatus is packaged or baled in transit or storage. Further, since hooks provide on two plates are configured to engaged with each other, which is advantageous in terms of manufacturing cost and space saving, there is a problem that the hooks cannot be locked due to creep deformation after repeated use.

DISCLOSURE OF THE INVENTION

The present invention is made to solve the above problem of a conventional body fluid suction reservoir, and its object is to provide a body fluid suction reservoir which has advantages that it is not bulky even if set to a patient and is superior in portability, and in which a lock is not easily released by external force in a state where it is packaged or baled in transit or storage.

In order to achieve the above object, according to a first aspect of the present invention, there is provided a body fluid suction reservoir including a flexible bag, two plates for supporting the bag, a spring put between the two plates, and a lock consisting of a hook, a release part and a member different from the two plates, by which lock the spring is held in a compressed state between the two plates, which held state can be released.

The above described lock may have flexibility. The lock can be held by one of the plates so as to be deformable from a first state in which the hook is engaged with the other plate to a second state in which the hook is not engaged, and the lock is urged to be in the first state.

The above described hook may be adapted to move in parallel with a surface of the one plate when the lock is deformed from the first state to the second state.

Also, a part of each of the above described plates may protrude in at least two locations around the release part of the lock in a direction opposite to a direction toward which the release part is pressed.

An engagement surface of the hook of the above described lock may have a portion protruding toward an engagement surface of the other plate on a tip side thereof, and the engagement face of the other plate may also have a portion protruding toward the engagement surface of the hook on a hole side.

Moreover, two or more of the above described springs may be arranged in a straight line in a longitudinal direction of the body fluid suction reservoir.

The above described bag may include a fluid evacuate port, a lid for the fluid evacuate port, and a suspension hole, and the lid for the fluid evacuate port may be provided with a holding part so as to be held by the suspension hole.

Further, according to a second aspect of the present invention, there is provides a body fluid suction reservoir including a flexible bag element having a fluid collecting port for taking in body fluid, a first plate and a second plate arranged in the bag element to face each other, an elastic member disposed between the first and second plates, and a lock body attached to the second plate, in which the lock body has a hook part and an operation part for displacing the lock portion (that is, a release part) so that the hook part is engaged with an engagement surface of the first plate to fix the first and second plates, thereby the elastic member is compressed and held between the first and second plates, and the operation part is operated to displace the hook part in parallel with a surface of the second plate, so that fixing of the first and second plates is released to generate negative pressure in the bag element.

The above described lock body may be elastically deformable. Moreover, a part of the lock body can be fixed to the second plate and thus, the operation part may be operated so as to displace at least the hook part in parallel with the surface of the second plate, and the hook part may be adapted to return to an initial position after the operation.

At least one of the first and second plates may have a cutout portion. Accordingly, the operation part may be disposed in the cutout portion or in correspondence with the cutout portion so as to be located inside an outline of the fluid suction reservoir.

The first plate may include a first shell part forming a part of the outline of the body fluid suction reservoir and a core part provided on a side of the shell part, which faces the second plate. Moreover, the second plate may include a second shell part forming a part of the outline of the body fluid suction reservoir. In this configuration, at least a part of the lock body is located on a side of the second shell facing the core part and thereby, the elastic member can be compressed and held by the core part and at least the part of the lock body.

In this case, it is possible to make the core part and the lock body harder than the first and second shell parts.

Alternatively, the first plate may include a first shell part forming a part of an outline of the body fluid suction reservoir and a first core part provided on a side of this shell part facing the second plate, and the second plate may include a second shell part forming a part of the outline of the body fluid suction reservoir and a second core part provided on a side of the shell part facing the first plate. The lock body may be attached to the second shell part or second core part, and the hook part is engaged with a surface of the first core part on an opposite side to the second plate (namely, with a hook engagement surface) to lock the first and second plates. Both ends of the elastic member are intervened between the first and second core parts and thereby the elastic member is held in a compressed state. According to this configuration, it is possible to make the first and second core parts harder than the first and second shell parts and therefore, constitute each part can be made from an appropriate material for each function, which makes possible to broaden the width of material selection.

Moreover, the above described lock body may have at least two hook parts, and the elastic member may be a spring.

The body fluid suction reservoir of the invention may have at least two springs arranged in a straight line between the first and second plates as an elastic member.

The bag element may have a fluid evacuate port, a lid for the fluid evacuate port, and a suspension hole, and the lid for the fluid evacuate port may be provided with a holding part for being held by the suspension hole. Alternatively, the bag element may have a holding part attachment hole for holding the holding part, separately from the suspension hole.

Other objects, features, and advantages of the present invention will become more apparent from the following description of embodiments of the present invention in connection with the accompanying drawings.

The present invention is specifically described in accordance with the drawings.

BEST MODE FOR CARRYING OUT THE INVENTION

Figure 1:
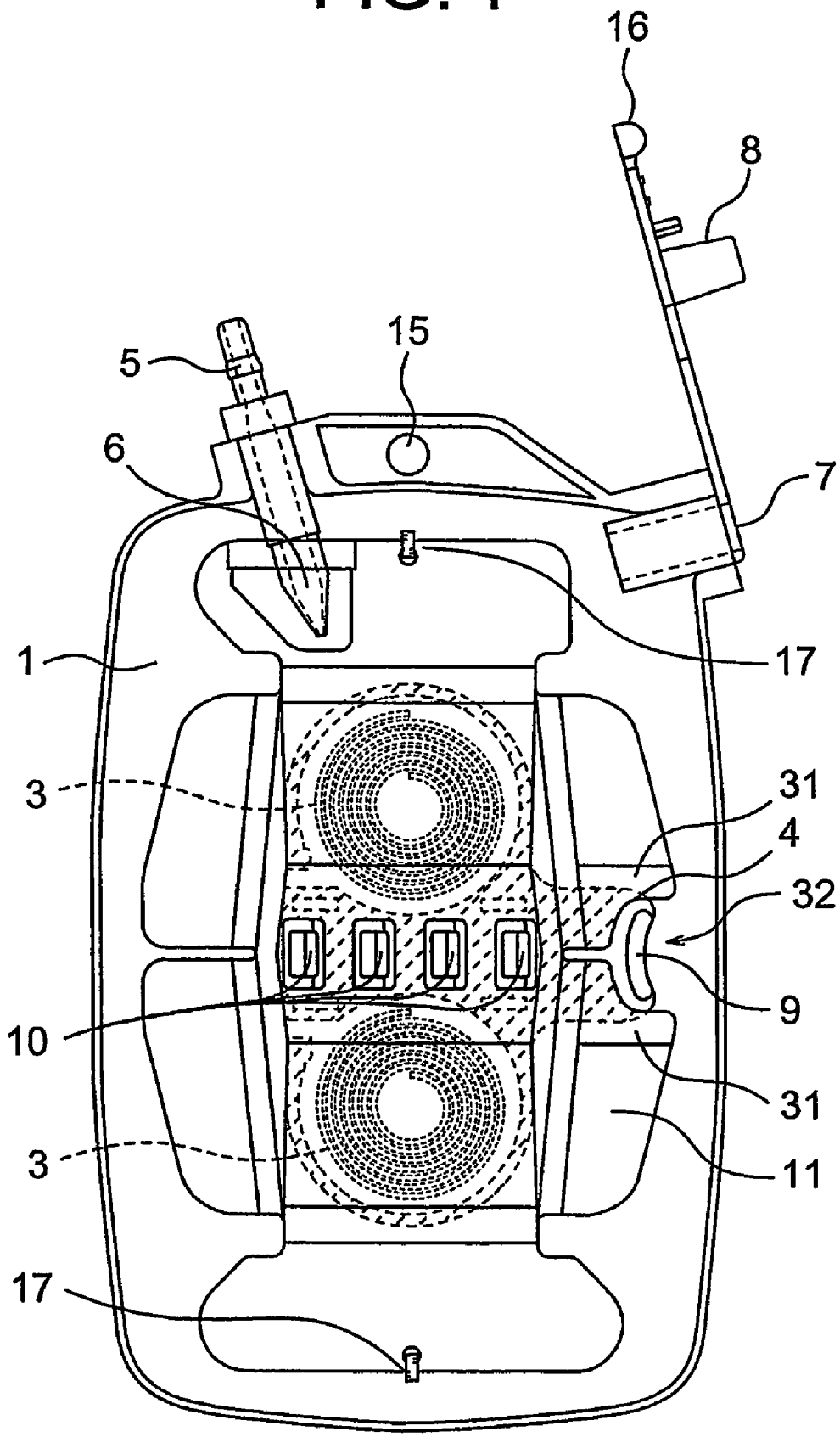
FIG. 1 is an outline view of a first embodiment of the present invention in an initial state.
Figure 5:
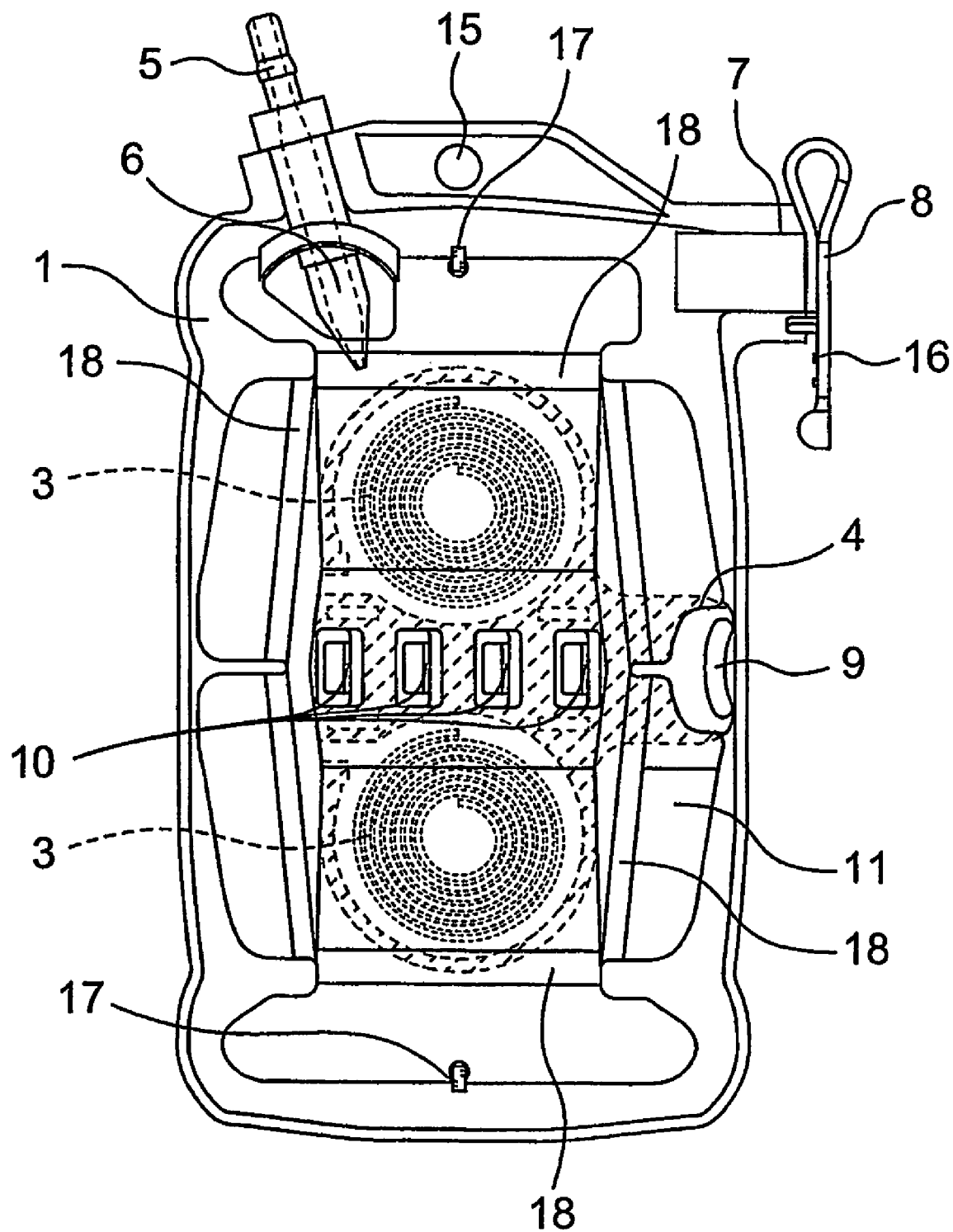
FIG. 5 is an outline view of the first embodiment of the present invention at the end of the suction.

According to a first embodiment of a body fluid suction reservoir of the present invention, as shown in FIG. 1, a fluid collecting port 5 is attached to pass through a bag 1, such that a drainage tube (not shown) kept in a patient is connected to the port 5. Preferably, the fluid collecting port 5 has a fluid collecting port one way valve 6 so that body fluid collected in the bag 1 does not flow back into a body cavity of the patient. In a similar manner, a fluid evacuate port 7 is provided to pass through the bag 1, and is provided with a lid 8 for the fluid evacuate port to be attached to the fluid evacuate port 7 during suction and collection (FIG. 3). Accordingly, when the suction and the collection are completed, the body fluid is evacuated by removing the fluid evacuate port lid 8 from the fluid evacuate port 7. As is understood from FIGS. 1 and 2, in a state before the suction and the collection of the body fluid, a spring 3, two plates (a first plate 11 and a second plate 12) holding the spring 3 therebetween, and a lock body 4 for locking the two plates in a state in which the spring 3 is compressed are arranged in the bag 1. It should be noted that, in FIGS. 1, 3, and 5, a transparent portion of the lock body 4 is made clear by drawing diagonal broken lines. Preferably, two or more of the springs 3 are arranged in a straight line in a longitudinal direction of the body fluid suction reservoir. This provides a slim shape, compared to a case of using one spring 3, in order to generate the same suction capacity and the suction pressure and accordingly, it is possible to make the body fluid suction reservoir easily enter a pocket when carrying it.

It is preferable that the spring 3 has a frustum shape, and can be folded up to a thickness one to three times larger than the diameter of a spring material without interference of a wire material of the spring, which realizes space saving in storage. Moreover, by forming the spring 3 into a shape of which winding pitch is gradually widened from a minor diameter side of the frustum to a major diameter side thereof, the non-linear property of the relation between load and deflection is restrained, which is more preferable for preventing suction pressure from being suddenly reduced at the beginning of the suction. Moreover, as a material of the spring 3, stainless steel which is not readily rust away is preferable. However, since it is not a portion directly contacting with a human body, the material is not restricted as long as the material has elasticity capable of ensuring sufficient suction force.

Figure 6:
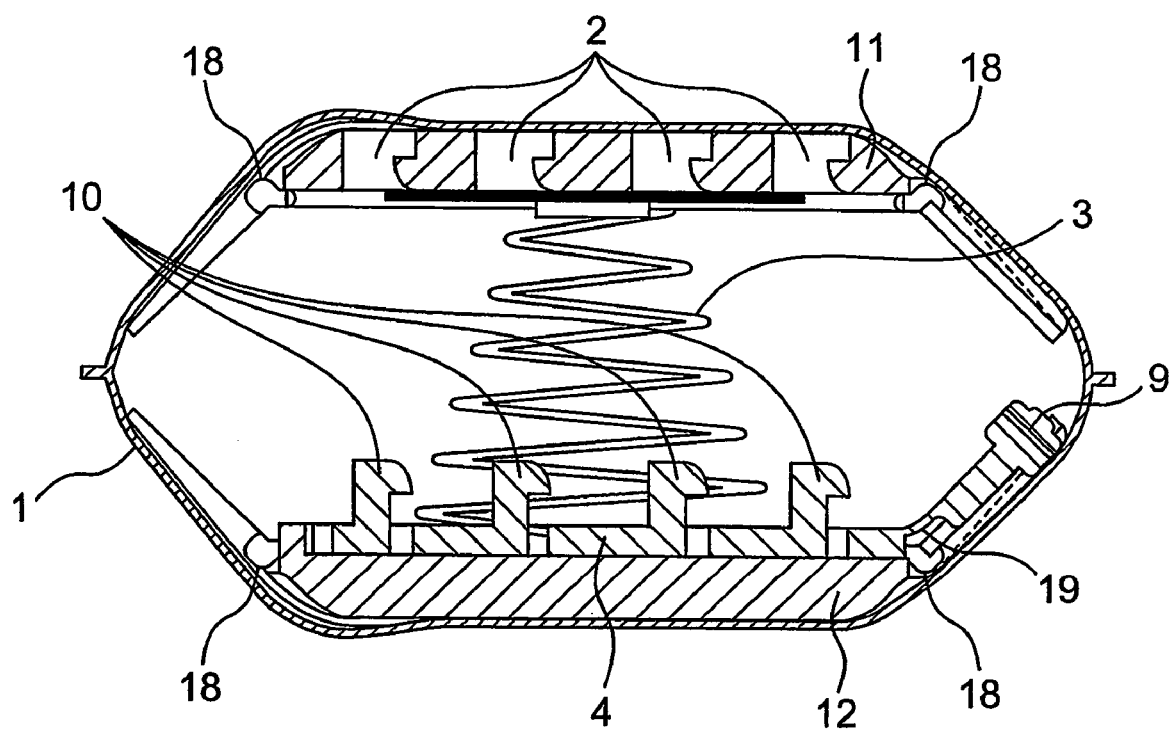
FIG. 6 is an enlarged sectional view of the central portion of the first embodiment of the preset invention at the end of the suction.

The lock body 4 is mounted on a surface of the second plate 12 on a side facing the first plate 11 by a well known method so that the lock body 4 can slide only in one direction on the surface. That is, the lock body 4 is held by the second plate 12 so that it can move in parallel with the surface of the plate, for example, it can move in a lateral direction but it is fixed in a vertical direction. The lock body 4 has four hooks 10 aligned in the above described lateral direction, that is, in a direction vertical to the longitudinal direction of the body fluid suction reservoir, and the hooks 10 extends vertically with respect to the surface of the second plate 12 so as to engage with an upward engagement surface 13 (FIGS. 6 and 7) formed in a hole 2 of the first plate 11, and thereby the first plate 11 and second plate 12 are locked.

The lock body 4 further includes a release part (or an operation part) 9 provided adjacently to one of the hooks 10. By pushing the release part 9 in the aligned direction of the hooks 10, the lock body 4 is slid (see FIG. 4) so that the first plate 11 and second plate 12 are unlocked. When the lock is released, the first plate 11 and second plate 12 are pushed by the spring 3 so as to increase the distance therebetween and thereby negative pressure is generated in the body fluid suction reservoir (FIGS. 3 to 6).

It is preferable that the first plate 11 and second plate 12 includes portions 31 which protrude in a direction opposite to a direction in which the release part 9 is pushed, in at least two locations around the release part 9 of the lock body 4. In other words, the protruded portions 31 form a cutout portion 32 on the first plate 11 and the second plate 12, and the release part 9 is housed correspondingly to the cutout portion 32. According to the above configuration, even if the body fluid suction reservoir falls to a floor, the protruded portions 31 of the plates contact with the floor firstly. Therefore, load is not directly applied to the release part 9 and therefore, the risk that the locked state is unexpectedly released is greatly reduced.

Figure 2:
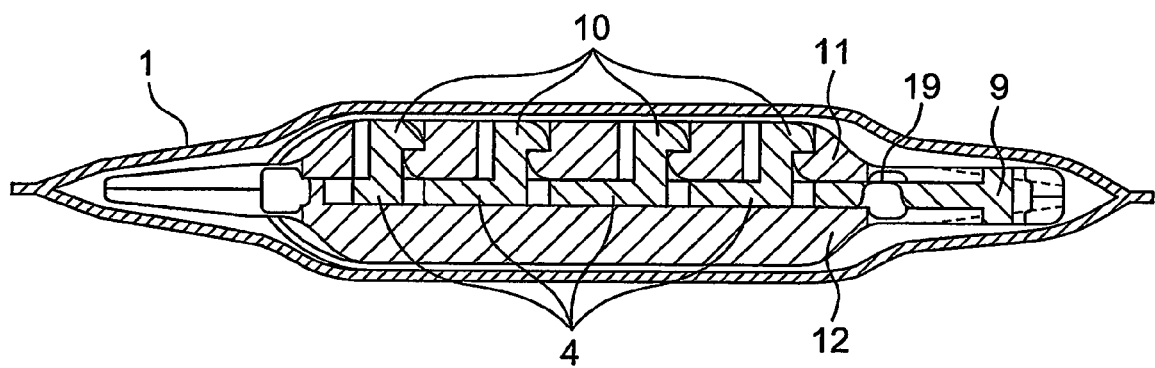
FIG. 2 is an enlarged sectional view of a central portion of the first embodiment of the present invention in the initial state.
Figure 3:
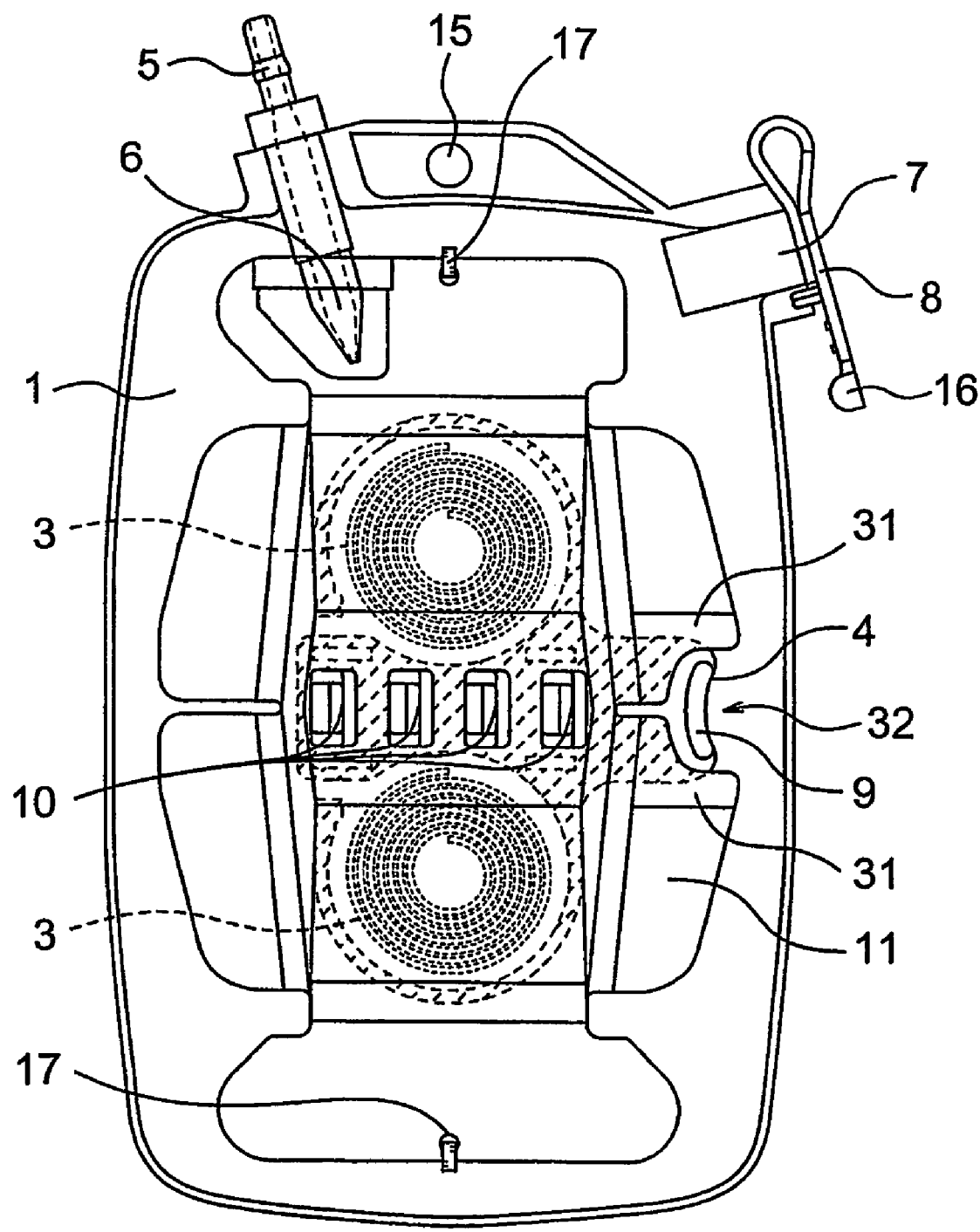
FIG. 3 is an outline view of the first embodiment of the present invention at the start of suction.

Moreover, it is preferable that the lock body 4 has flexibility (or elasticity) by which the lock body 4 can be deformed from a state in which the hooks 10 are secured to the first plate 11 as shown in FIG. 2 to a state in which the hooks 10 are not secured to the plate 11. On the other hand, the lock body 4 is required to have strength for locking the first plate 11 and the second plate 12 in a state in which the spring 3 is compressed. Therefore, when forming the lock body 4 as a single component, it is preferable to use high-rigidity engineering plastic, such as polyacetal or the like, as a material of the lock body 4. Since the lock body 4 has elasticity, the hooks 10 is adapted to receive force (return force) which urges the hooks 10 in a direction so as to engage with the first plate 11.

Both the first plate 11 and the second plate 12 have thin-plate portions 18 (FIGS. 5 and 6), and are constituted so as to be bent by the thin-plate portions 18 serving as a fulcrum in accordance with the extension of the spring 3. Also, the lock body 4 has a thin-lock portion 19 which is bent correspondingly to the bend of the thin-plate portions 18. In order to further decrease the risk that the thin-lock portion 19 is cracked, it is preferable to separate the release part 9 from other portions of the lock body 4, that is, to form the structure so as not to include the thin-lock portion 19 by connecting the lock body 4 with the release part 9 like a hinge. Alternatively, it is preferable to use a material which has large breaking elongation and is not easily cracked for the release part 9 having the thin-lock portion 19, and to connect the thin-lock portion 19 to the lock 4 made of high-rigidity engineering plastic by means of fitting or the like.

Figure 7:
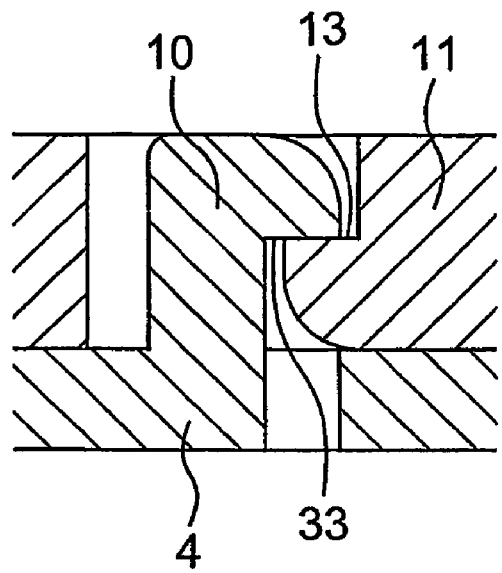
FIG. 7 is an enlarged sectional view of a hook and a part of a first plate of the first embodiment of the present invention in the initial state.
Figure 8:
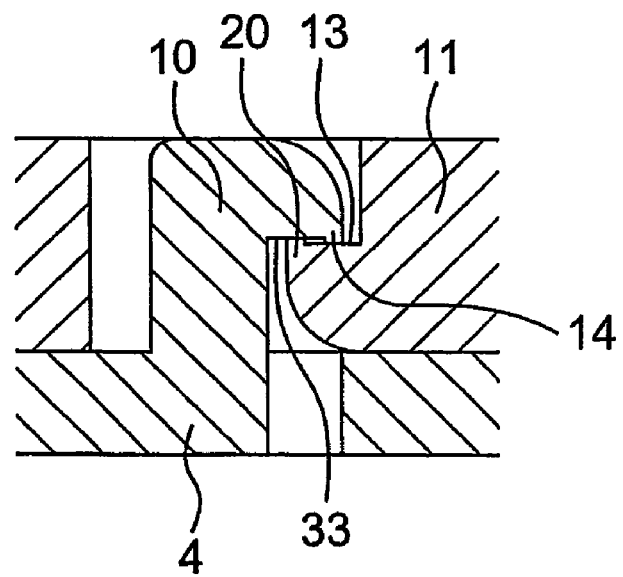
FIG. 8 is an enlarged sectional view of the hook and another example of the part of the first plate of the first embodiment of the present invention in the initial state.

Moreover, as shown in FIG. 7, the engagement surface 33 of the hook 10 may contact with the engagement surface 13 of the first plate 11 in parallel, however, by forming a protruded portion on front ends 20 and 14 of the engagement surfaces 13 and 33 as shown in FIG. 8, the risk of release of the lock body 4 in transit or storage can be further reduced.

Figure 9:
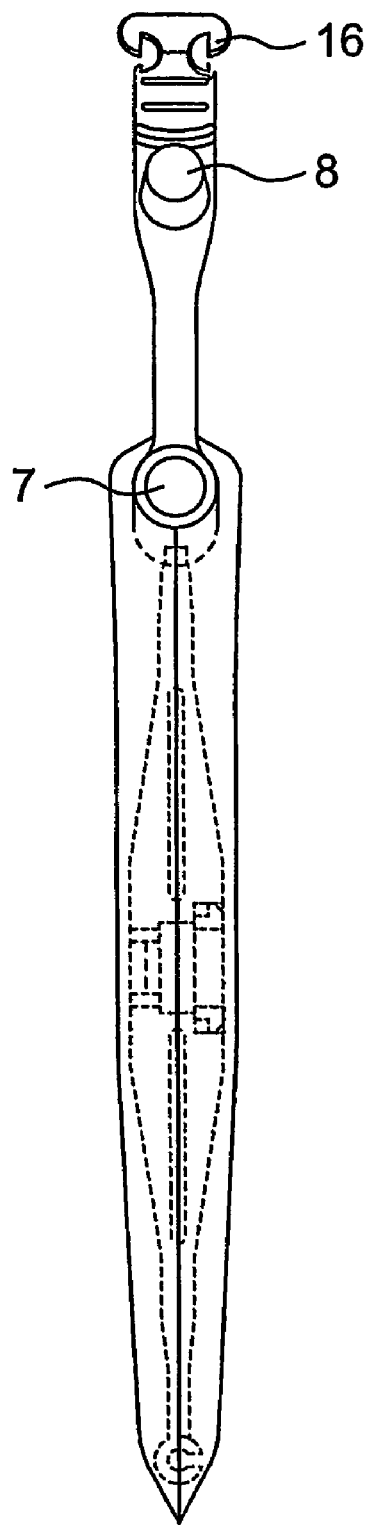
FIG. 9 is a side view of an outline view of the first embodiment of the present invention in the initial state.
Figure 10:
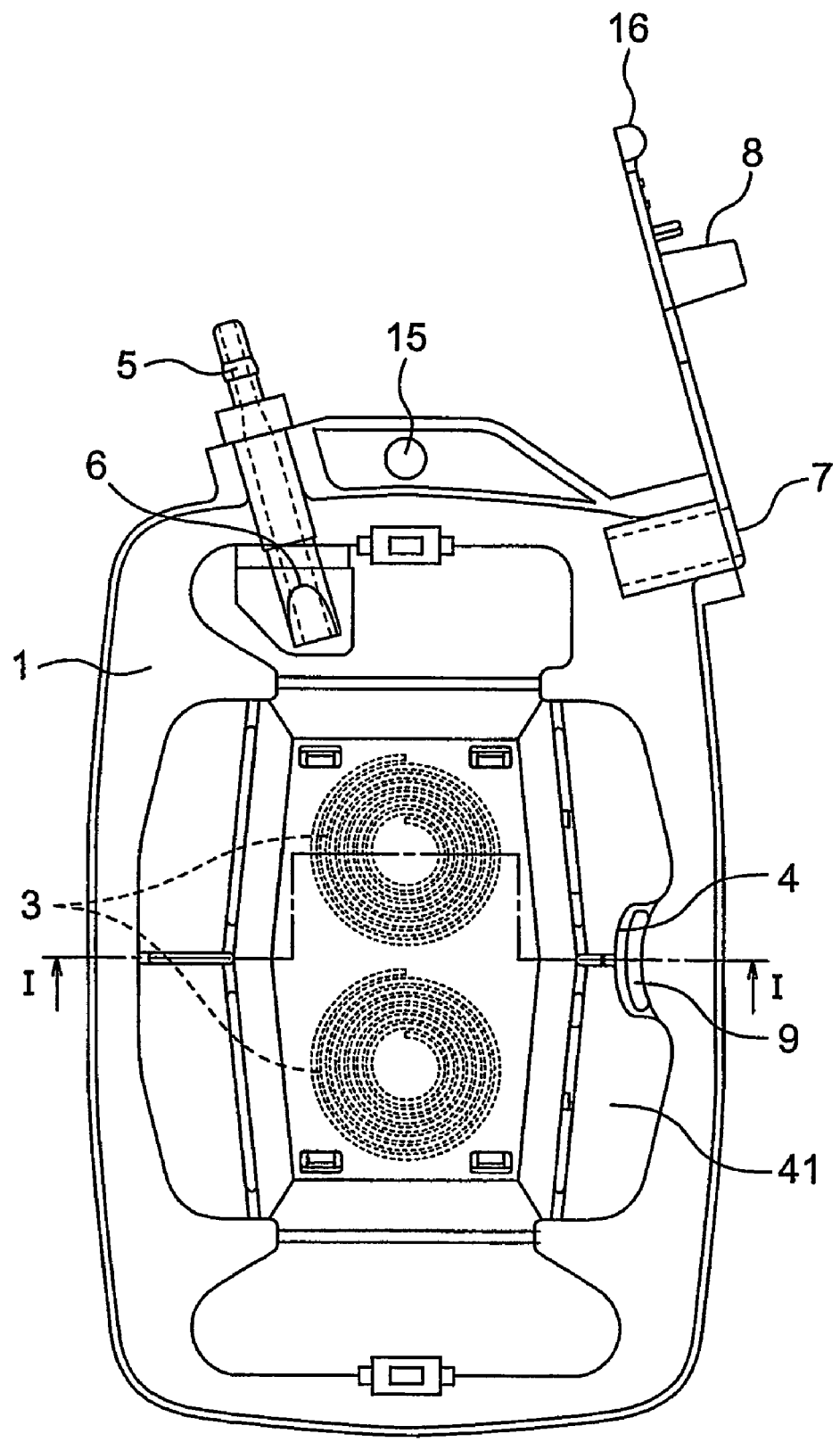
FIG. 10 is an outline view of a second embodiment of the present invention in an initial state.
Figure 16:
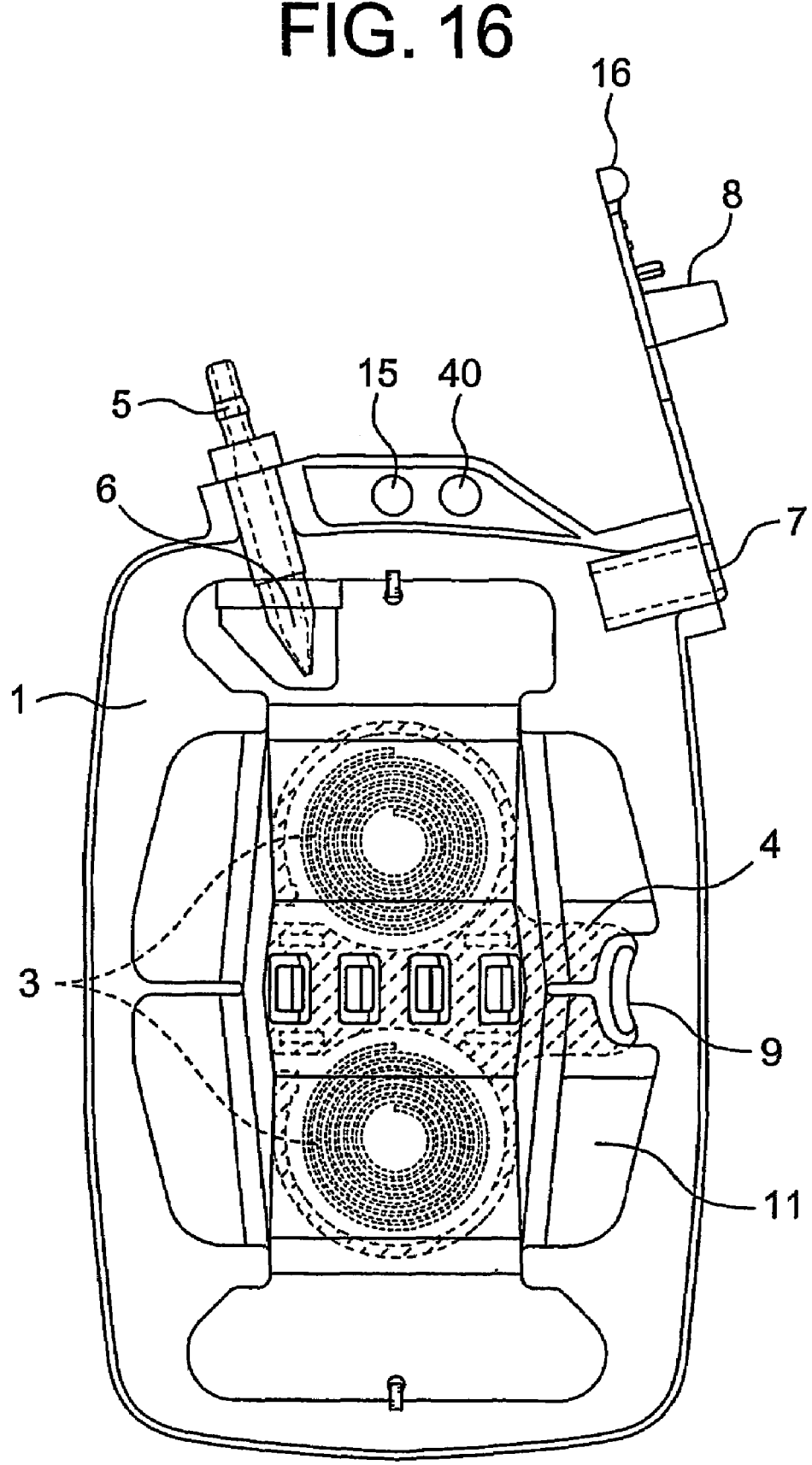
FIG. 16 is an outline view of a third embodiment of the present invention in an initial state.

As shown in FIGS. 1 and 9, a holding part 16 may be provided adjacently to the fluid evacuate port lid 8 to fix the holding part 16 by hooking the holding part 16 to a suspension hole 15 of the bag 1, which is further preferable since the fluid evacuate port lid 8 does not get in the way when evacuating the fluid. Alternatively, as shown in FIG. 16, the bag 1 may have a holding part attachment hole 40 for fixing the holding part 16, in addition to the suspension hole 15.

The first plate 11 and the second plate 12 may be connected each other so as to be pivotable by means of a plate connecting member 17.

Figure 4:
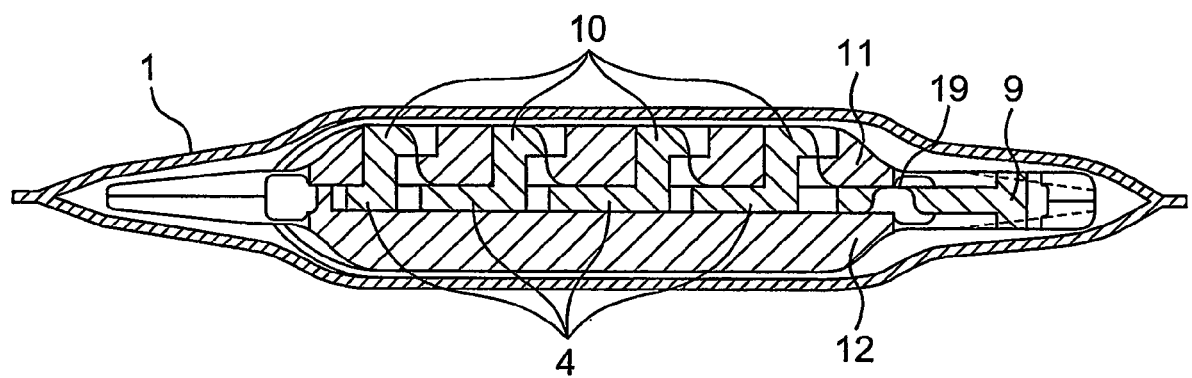
FIG. 4 is an enlarged sectional view of the central portion of the first embodiment of the present invention at the start of the suction.

As a method of using the body fluid suction reservoir of the present invention, firstly, the fluid evacuate port 7 is closed using the fluid evacuate port lid 8 to connect a drainage tube set to a patient to the fluid collecting port 5. Then, as shown in FIGS. 3 and 4, the release part 9 of the lock body 4 is inserted toward a center of the fluid suction reservoir to release the engagement of the hooks 10 with the first plate 11. At this stage, force for separating the first plate 11 and the second plate 12 from each other acts therein due to resilience of the spring 3, so that negative pressure is generated in the bag 1. By this negative pressure, body fluid of the patient is sucked and collected from a body cavity. After the suction and the collection of the body fluid are completed, the fluid evacuate port lid 8 is opened to discard the waste fluid stored in the bag 1. Additionally, the lock body 4 may be flexible so that the hooks are urged in a direction (in a right direction in the drawings) to engage with the first plate 11 and thus, it is possible to press the first plate 11 and the second plate 12 to compress the spring 3 to return to the initial state shown FIG. 1 for re-suction.

As a property requested for the first plate 11 and the second plate 12, it is raised that the first plate 11 and the second plate 12 have rigidity (high elastic modulus, creep resistance) for sufficiently resisting the stress of the compressed spring 3 for a long time, and are translucent or transparent for confirming condition and quantity of the contents, and further, it is important that the thin-plate portions 18 are not easily cracked (breaking elongation is large). In view of these requested physical properties, high molecular weight polypropylene is most preferable as a material constituting the first plate 11 and second plate 12 as a single component, respectively.

FIGS. 10 to 15 show a second embodiment of the body fluid suction reservoir of the present invention. The second embodiment is different from the first embodiment in that each of the first plate 11 and the second plate 12 has a shell part made of a material which is comparatively soft and has large breaking elongation. In FIGS. 10 to 15, a component similar to that of the first embodiment is indicated by the same reference number.

Figure 11:
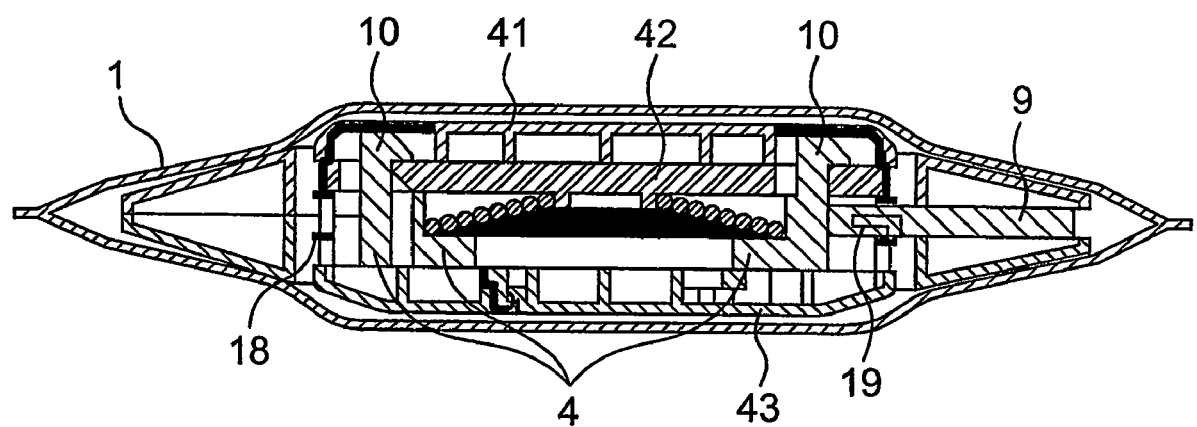
FIG. 11 is an enlarged sectional view of the second embodiment of the present invention in the initial state, taken along line I-I in FIG. 10.
Figure 12:
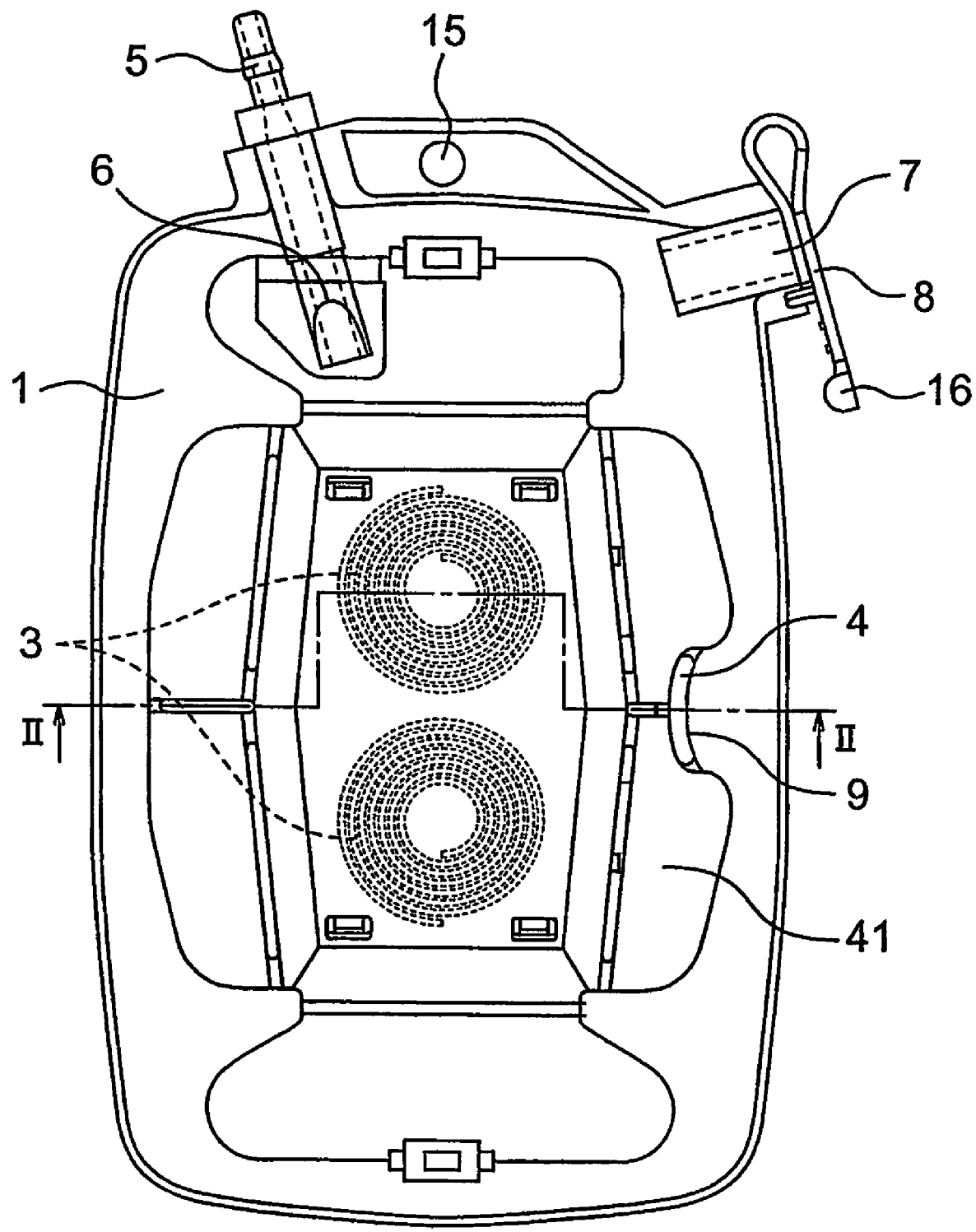
FIG. 12 is an outline view of the second embodiment of the present invention at the start of suction.
Figure 13:
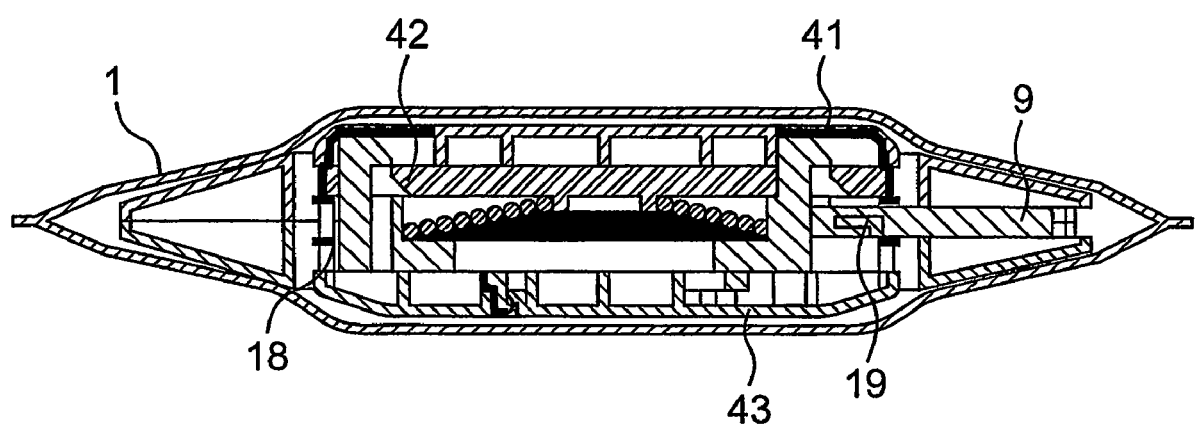
FIG. 13 is an enlarged sectional view of the second embodiment of the present invention at the start of the suction, taken along line II-II in FIG. 12.
Figure 14:
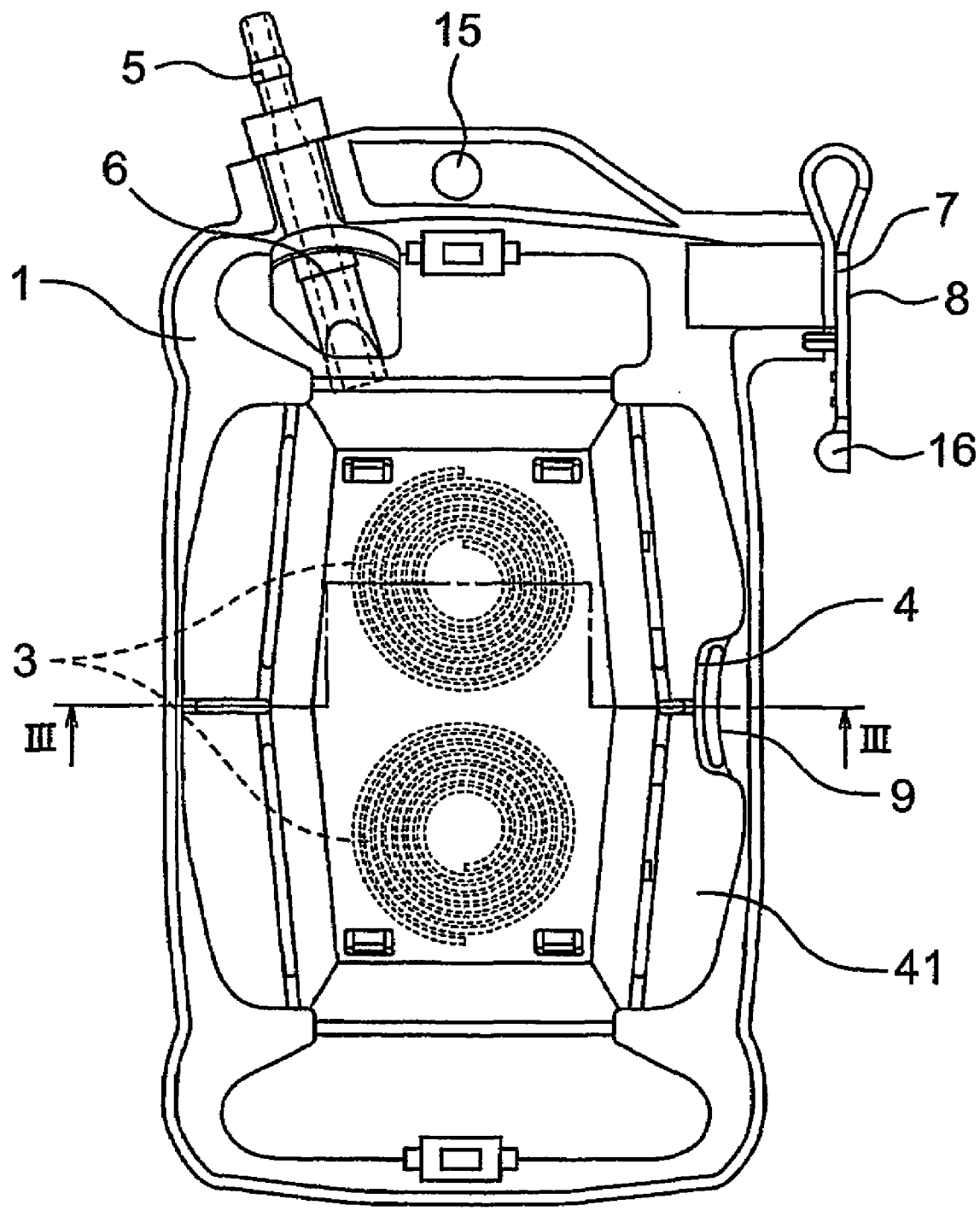
FIG. 14 is an outline view of the second embodiment of the present invention at the end of the suction.
Figure 15:
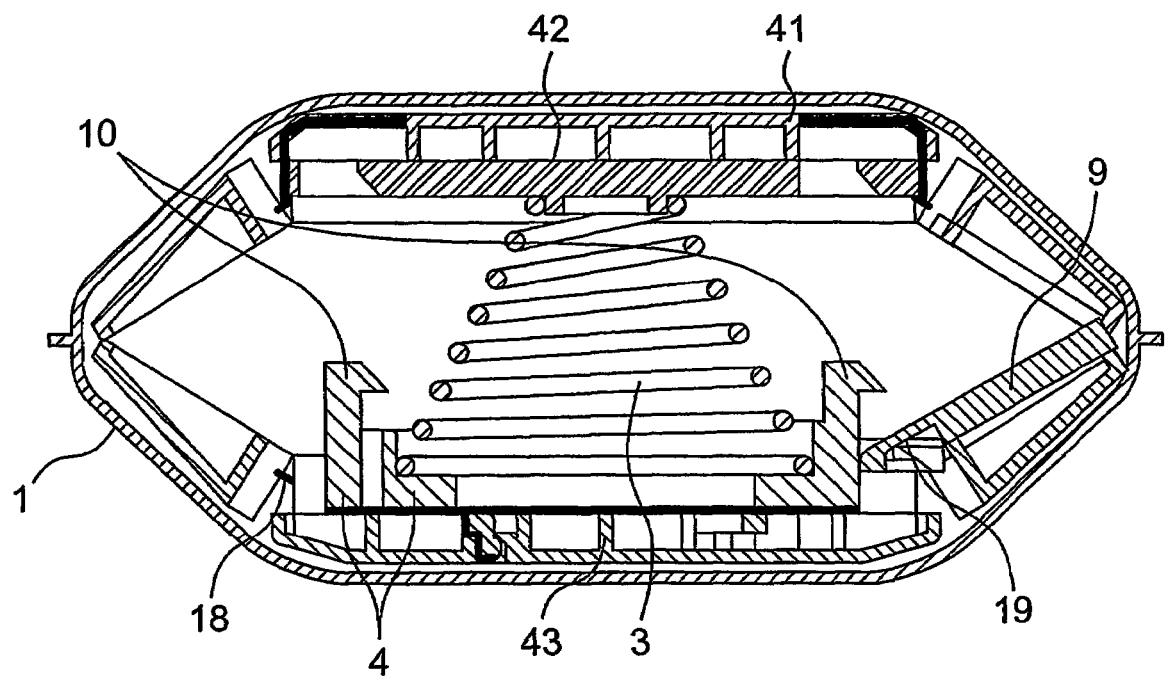
FIG. 15 is an enlarged sectional view of the second embodiment of the present invention at the end of the suction, taken along line III-III in FIG. 14.

As is understood from FIG. 11, in the case of the second embodiment, a first plate is constituted by a shell part 41 which serves to hold an outline of the body fluid suction reservoir, and a core part 42 fixed on an inner side of the shell part 41 which core part 42 serves to directly receive the stress of the spring 3. The shell part 41 is provided with a thin-plate portion 18 (FIG. 15). The hooks 10 of the lock body 4 are engaged with an upper surface of the core part 42 to lock the first plate and the second plate as with the case of the first embodiment. By using a different component for each function like this, it becomes possible to constitute each part by a material suitable for each function, which makes it possible to broaden the width of material selection.

On the other hand, the second plate 12 is constituted only by a shell part 43 serving to keep the outline of the body fluid suction reservoir so that the lock body 4 attached to the shell part 43 directly supports the spring 3. The lock body 4 of the second embodiment extends on the second plate over a wide area compared to the case of the lock body 4 of the first embodiment. Accordingly, it is unnecessary to set the hooks 10 in a central portion of the body fluid suction reservoir, and as shown in FIG. 11, it is possible to set two hooks 10 around each spring 3. This structure in which the lock body 4 supports the spring 3 is advantageous because the number of components can be further reduced and the cost can be suppressed. Accordingly, the spring 3 is held by the core part 42 and the lock body 4 in a compressed state.

The engineering plastic having high elastic modulus and creep resistance as used for the first plate 11 and the second plate 12 of the first embodiment is normally crystalline plastic or fiber reinforced plastic which is opaque and has small breaking elongation. However, amorphous plastic which is transparent and has large breaking elongation has small rigidity in general, and thus, it is preferable to use, as a material of the core part 42, engineering plastic such as polyacetal, filler reinforced plastic, fiber reinforced plastic and the like, which have high elasticity and creep resistance, or metal such as aluminum or stainless steel, and to use, as a material of the shell part 41 provided with the thin-plate portion 18, plastic such as polyethylene or polypropylene having transparency and large breaking elongation.

FIGS. 16 to 21 show a third embodiment of the body fluid suction reservoir of the present invention. The third embodiment is different from the first embodiment in that a first plate 11 and a second plate 12 are constituted by shell parts 41 and 43 made of a material which is comparatively soft and has large breaking elongation, and hard core parts 42 and 44 fixed on inner surfaces of the shell parts to directly receive the stress of springs 3, respectively. In FIGS. 16 to 21, a component similar to that of the first and second embodiments is indicated by the same reference number with those.

Figure 17:
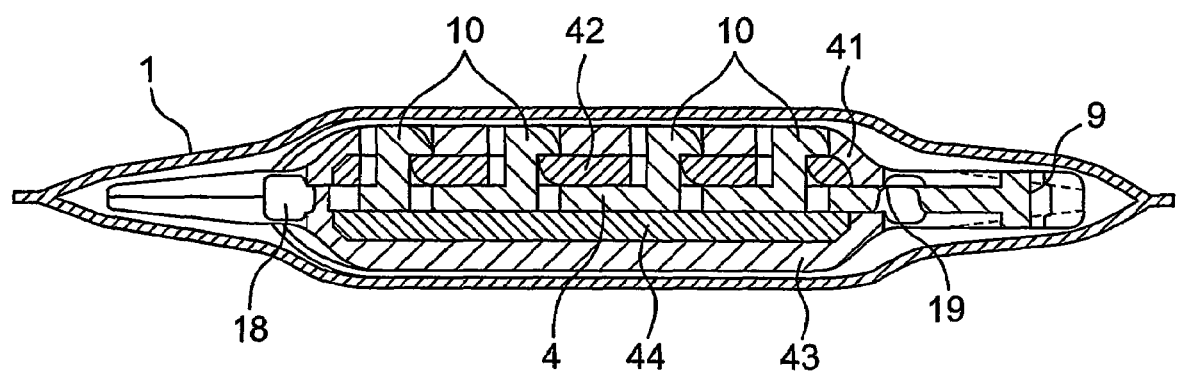
FIG. 17 is an enlarged sectional view of a central portion of the third embodiment of the present invention in the initial state.
Figure 18:
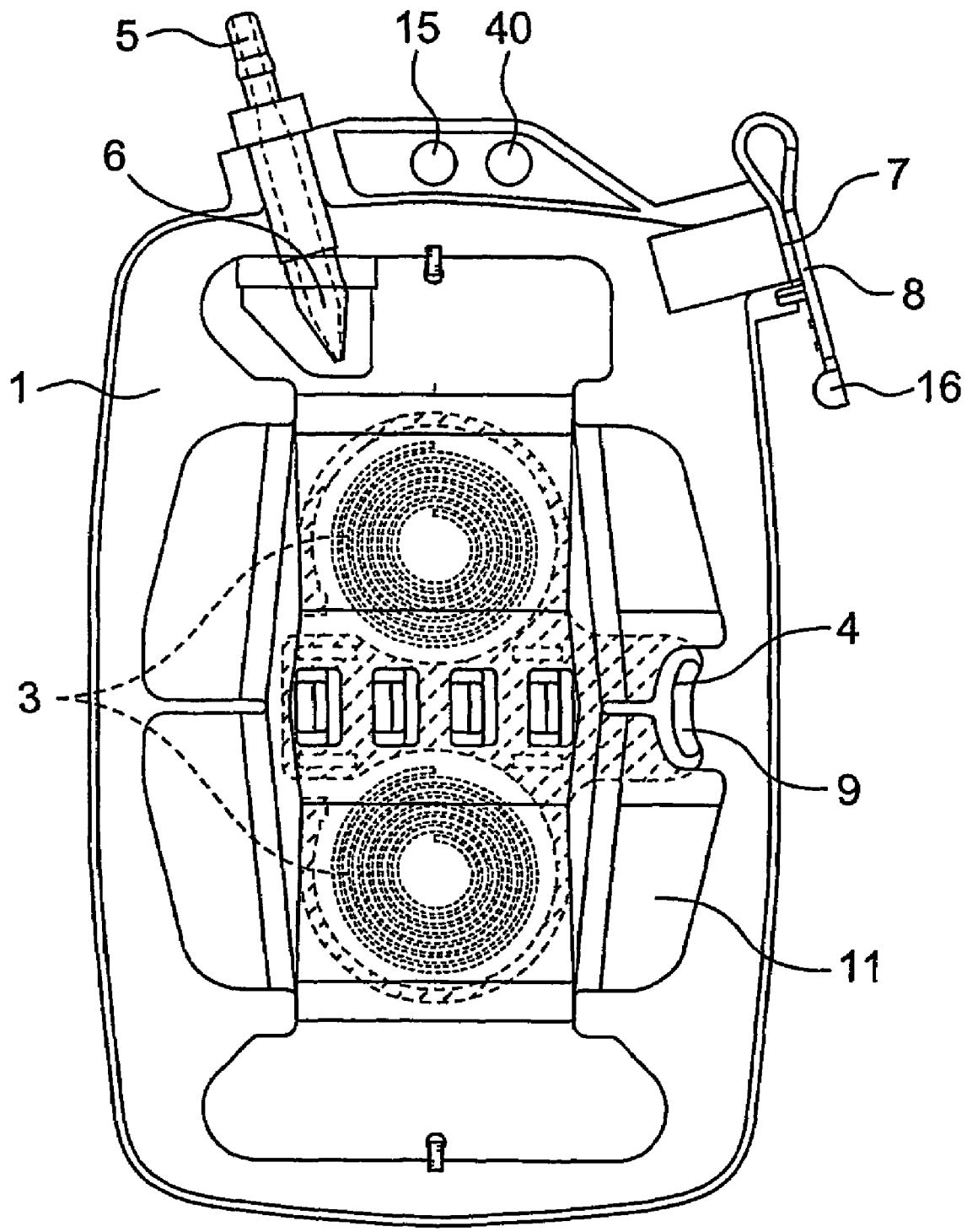
FIG. 18 is an outline view of the third embodiment of the present invention at the start of suction.
Figure 19:
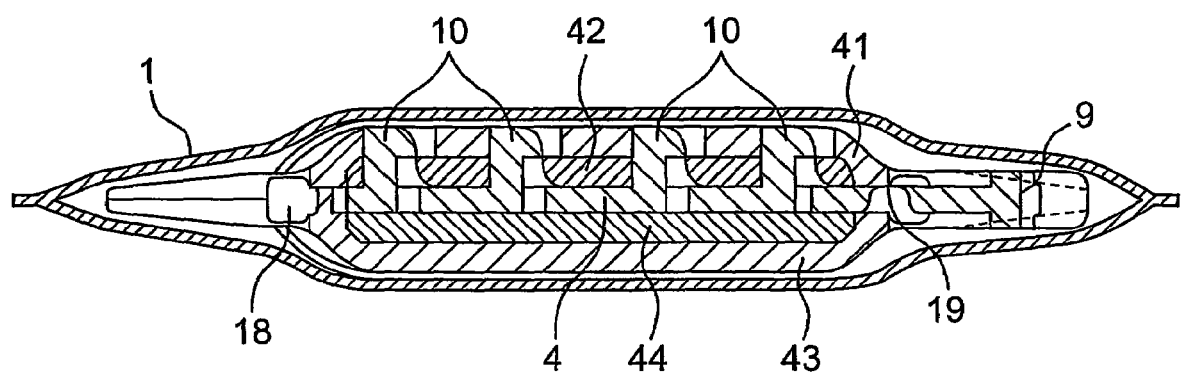
FIG. 19 is an enlarged sectional view of the central portion of the third embodiment of the present invention at the start of the suction.
Figure 20:
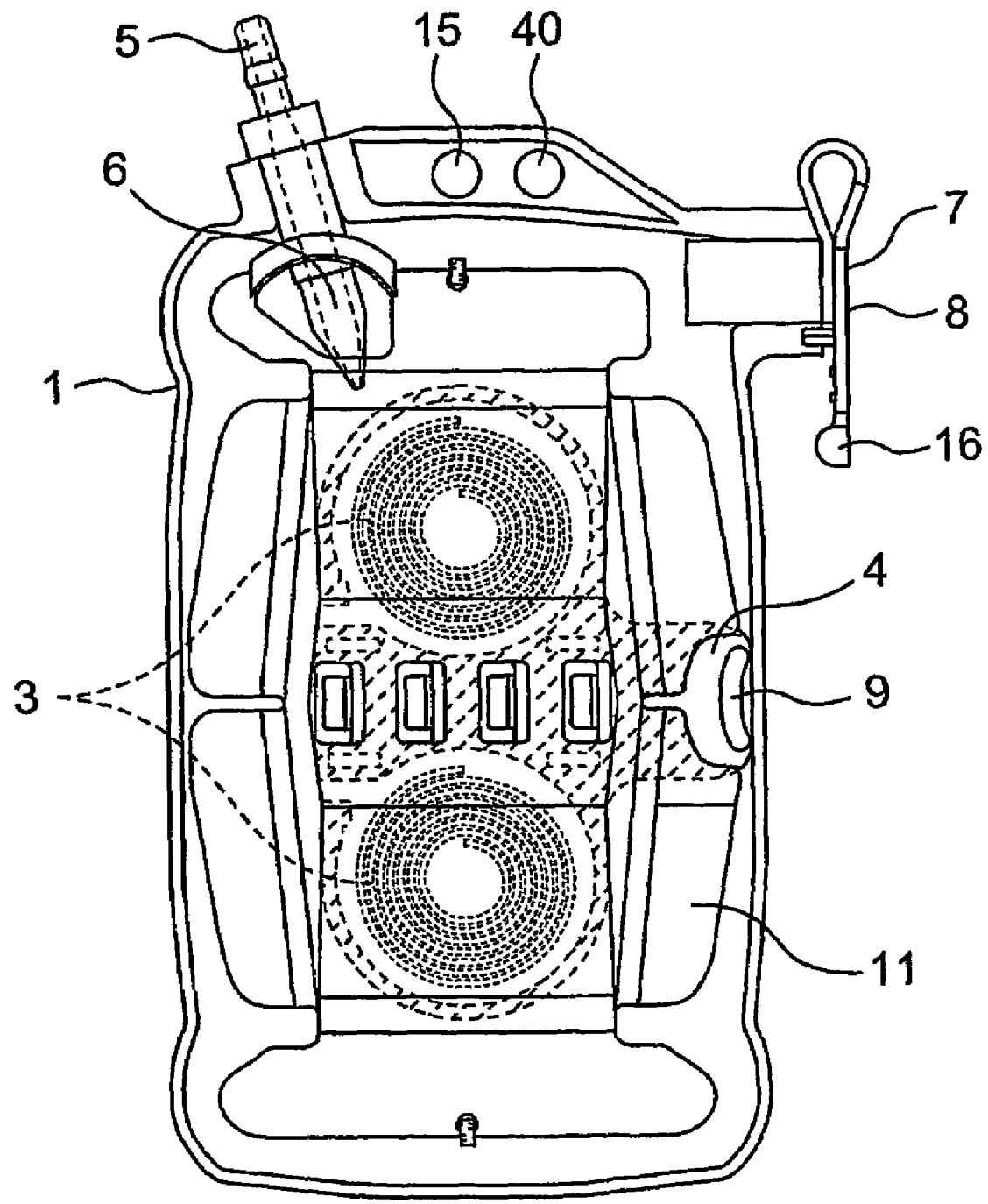
FIG. 20 is an outline view of the third embodiment of the present invention at the end of the suction.
Figure 21:
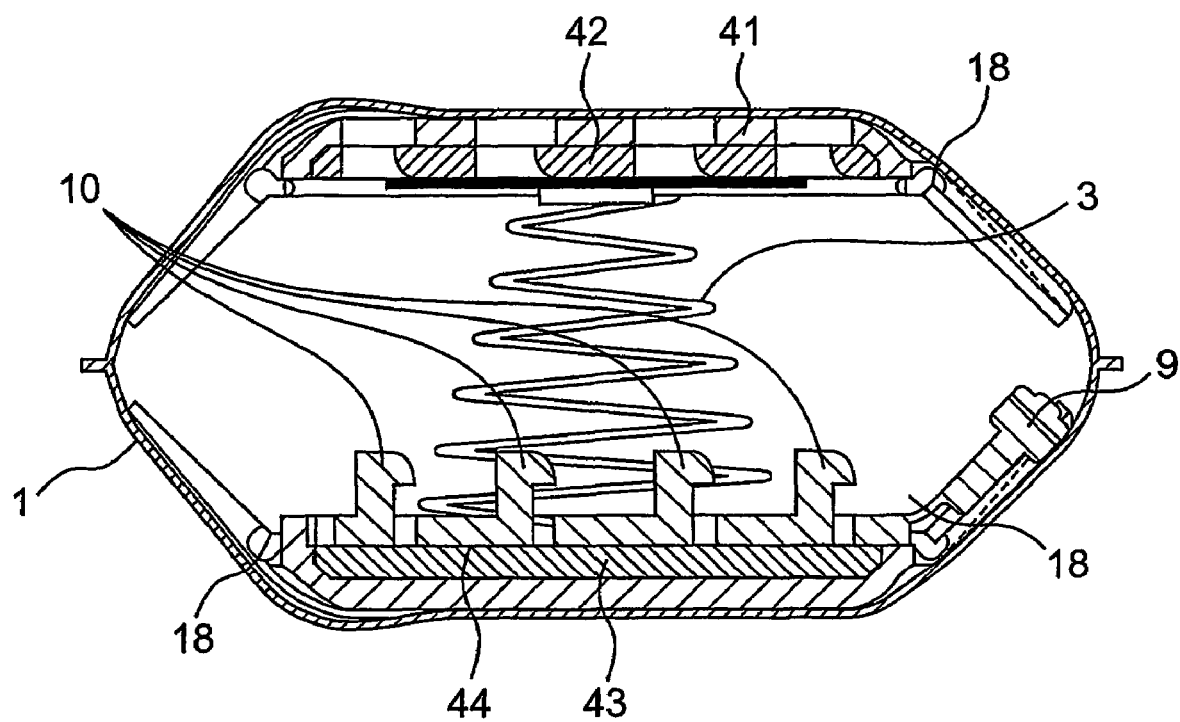
FIG. 21 is an enlarged sectional view of the central portion of the third embodiment of the present invention at the end of the suction.

As shown in FIG. 17, the first plate is constituted by the shell part 41 serving to keep an outline of the body fluid suction reservoir, and the core part 42 serving to directly receive the stress of the springs 3, and hooks 10 of a lock body 4 are engaged with an upper surface of the core part 42. In the case of the third embodiment, the second plate is also constituted by the shell part 43 serving to keep the outline of the body fluid suction reservoir, and the core part 44 serving to directly receive the stress of the springs 3. In other words, in the case of the third embodiment, the first plate 11 of the first embodiment shown in FIG. 2 is constituted by the shell part 41 and the core part 42, and the second plate 12 of the first embodiment is constituted by the shell part 43 and the core part 44.

Thus, by constituting the first plate and the second plate by completely different components for each function, it is possible to constitute each part by a material suitable for each function, which makes it possible to broaden the width of material selection. That is, in the case of the third embodiment, since the springs 3 are supported by the core parts 42 and 44, it becomes possible that only the core parts 42 and 43 are constitute by a hard material.

Accordingly, similarly to the case of the second embodiment, it is preferable to use the engineering plastic such as polyacetal, filler reinforced plastic, fiber reinforced plastic and the like which have high elastic modulus and creep resistance, or metal such as aluminum or stainless steel as a material of the core parts 42 and 44, and to use plastic such as polyethylene or polypropylene having transparency and large breaking elongation as a material of the shell parts 41 and 43.

In the case of the third embodiment, since the core parts 42 and 43 support the springs 3, load in a direction vertical to surfaces of the plates does not directly act on the lock body 4 from the spring 3 and thus, it is possible to slide the lock body 4 on the second plate, smoother.

Although the above descriptions are made for embodiments, the present invention is not limited to the embodiments. It is apparent for a person skilled in the art that the present invention can be modified or corrected within the scope of the spirit and attached claims of the present invention.

The invention claimed is:

1. A body fluid suction reservoir comprising:
    a bag element having a fluid collecting port for taking in body fluid;
    a first plate and a second plate arranged in the bag element so as to face each other;
    an elastic member disposed between the first plate and the second plate; and
    a lock body attached to the second plate, wherein
    the lock body comprises a hook part and an operation part for displacing the hook part,
    the hook part is adapted to engage with a hook engagement surface of the first plate to fix the first plate and the second plate, so that the elastic member is compressed and held between the first plate and the second plate,
    the operation part is operated to displace the hook part in parallel with a surface of the second plate, so that fixing of the first plate and the second plate are released to generate negative pressure in the bag elements,
    the first plate comprises a first shell part forming a part of an outline of the body fluid suction reservoir, and a core part provided on a side of the shell part facing the second plate,
    the second plate comprises a second shell part forming a part of the outline of the body fluid suction reservoir,
    at least a part of the lock body is located on a side of the second shell part facing the core part, so that the elastic member is compressed and held by the core part and at least the part of the lock body, and
    the core part and the lock body comprise material having higher hardness than the first shell part and the second shell part.

2. The body fluid suction reservoir according to claim 1, characterized in that the lock body is elastically deformable, a part of the lock body is fixed to the second plate, thereby the operation part is operated so as to displace at least the hook part in parallel with the surface of the second plate, and the hook part returns to an initial position after the operation.

3. The body fluid suction reservoir according to claim 1, characterized in that at least one of the first plate and the second plate comprises a cutout portion, and the operation part is located in the cutout portion or in correspondence with the cutout portion, so as to be positioned inside an outline of the body fluid suction reservoir.

4. The body fluid suction reservoir according to claim 1, wherein
    the first plate comprises a first shell part forming a part of an outline of the body fluid suction reservoir, and a first core part provided on a side of the first shell part facing the second plate, the second plate comprises a second shell part forming a part of the outline of the body fluid suction reservoir, and a second core part provided on a side of the second shell part facing the first plate, the hook engagement surface is configured by a surface of the first core part located on an opposite side to the second plate, and the elastic member is compressed and held by the first core part and the second core part.

5. The body fluid suction reservoir according to claim 1, wherein the first core part and the second core part are harder than the first shell part and the second shell part.

6. The body fluid suction reservoir according to claim 5, comprising at least two springs arranged in a straight line between the first plate and the second plate.

7. The body fluid suction reservoir according to claim 1, wherein the lock body comprises at least two hook parts.

8. The body fluid suction reservoir according to claim 1, wherein the elastic member is a spring.

9. The body fluid suction reservoir according to claim 1, wherein the bag element comprises a fluid evacuate port for evacuating the body fluid, a lid for the fluid evacuate port, and a suspension hole or a holding part attachment hole, and the lid for the fluid evacuate port is provided with a holding part to be held by the suspension hole or the holding part attachment hole.

* * * * *